United States Patent [19]

Förster et al.

[11] Patent Number: 4,549,899
[45] Date of Patent: Oct. 29, 1985

[54] HERICIDALLY ACTIVE NOVEL SUBSTITUTED 3-TRIHALOGENOMETHYL-1,2,4-THIADIAZOL-5-YL-OXYACETAMIDES

[75] Inventors: Heinz Förster, Wuppertal; Erich Klauke, Odenthal; Ludwig Eue, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 516,177

[22] Filed: Jul. 20, 1983

[30] Foreign Application Priority Data

Jul. 28, 1982 [DE] Fed. Rep. of Germany ....... 3228147

[51] Int. Cl.[4] .................. C07D 285/08; A01N 43/82
[52] U.S. Cl. .................. 71/90; 260/239 BF; 544/134; 546/146; 546/164; 546/165; 546/208; 548/129
[58] Field of Search ............. 71/90; 548/129; 260/239 BF; 544/134; 546/146, 164, 165, 208

[56] References Cited

U.S. PATENT DOCUMENTS 3,260,725  7/1966  Schroeder .............. 548/129
4,204,857  5/1980  Rothgery .............. 548/129
4,228,290 10/1980  Rothgery .
4,408,055 10/1983  Forster ............... 548/129

FOREIGN PATENT DOCUMENTS 3038636  5/1982  Fed. Rep. of Germany ...... 548/129
80/2020  7/1981  South Africa ................ 548/129

OTHER PUBLICATIONS

Title Page of German DE No. 30 04 326, dated 2/6/80, and Title Page of German DE No. 29 14 003, dated 10/16/80.

Primary Examiner—Robert Gerstl
Attorney, Agent, or Firm—Sprung, Horn, Kramer & Woods

[57] ABSTRACT

A substituted 3-trihalogenomethyl-1,2,4-thiadiazol-5-yl-oxyacetamide of the formula

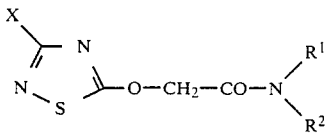

in which x represents $-CFCl_2$, $-CF_2Cl$ or $-CF_3$ and $R^1$ and $R^2$ are identical or different and individually represent optionally substituted alkyl, alkenyl, alkinyl, alkoxy, aralkyl, cycloalkyl, cycloalkenyl, aryl or a nitrogen-containing heterocyclic radical, or, together with the nitrogen atom to which they are bonded, form an optionally substituted, optionally partially unsaturated and optionally benzofused monocyclic or bicyclic structure which optionally contains further hetero atoms, which possesses herbicidal activity.

8 Claims, No Drawings

HERBICIDALLY ACTIVE NOVEL SUBSTITUTED 3-TRIHALOGENOMETHYL-1,2,4-THIADIAZOL-5-YL-OXYACETAMIDES

The invention relates to new substituted fluorine-containing 3-trihalogenomethyl-1,2,4-thiadiazol-5-yl-oxyacetamides, a process for their preparation and their use as herbicides.

It is already known that certain azolyloxycarboxamides can be used as herbicides (see, for example, DE-OS (German Published Specification) No. 2,914,003 and DE-OS (German Published Specification) No. 3,004,326). Thus, for example, 4,5-dichloro-1,3-thiazol-2-yl-oxyacetic acid N,N-diethylamide can be employed for selectively combating grasses in dicotyledon crop plants, such as, for example, cotton; however, the compound is not sufficiently effective against dicotyledon weeds.

New substituted fluorine-containing 3-trihalogenomethyl-1,2,4-thiadiazol-5-yl-oxyacetamides of the formula

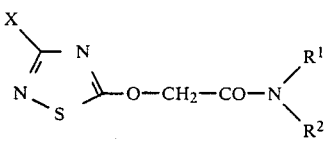

in which

X represents —CFCl$_2$, —CF$_2$Cl or —CF$_3$ and

R$^1$ and R$^2$ are identical or different and individually represent optionally substituted alkyl, alkenyl, alkinyl, alkoxy, aralkyl, cycloalkyl, cycloalkenyl, aryl or a nitrogen-containing heterocyclic radical, or, together with the nitrogen atom at which they are found, form an optionally substituted, optionally partially unsaturated and optionally benzofused monocyclic or bicyclic structure which optionally contains further hetero atoms, have not been found.

The new compounds of the formula (I) are obtained when hydroxyacetamides of the formula

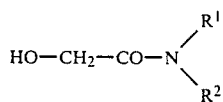

in which R$^1$ and R$^2$ have the meaning given above, are reacted with a fluorine-containing 5-chloro-3-trihalogenomethyl-1,2,4-thiadiazole of the formula

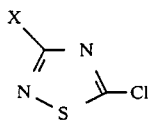

in which X has the meaning given above, in the presence of an acid acceptor and, if appropriate, using a diluent.

The new substituted fluorine-containing 3-trihalogenomethyl-1,2,4-thiadiazol-5-yl-oxyacetamides of the formula (I) are distinguished by powerful herbicidal activity.

Surprisingly, the active compounds according to the invention of the formula (I), are very effective against grasses as well as against dicotyledon weeds. The new active compounds hence possess substantial advantages over the previously known azolyloxycarboxamides (according to DE-OS (German Published Specifications) Nos. 2,914,003 and 3,004,326), which are effective essentially only against grasses.

The invention preferably relates to 3-trihalogenomethyl-1,2,4-thiadiazol-5-yl-oxyacetamides of the formula (I) in which R$^1$ and R$^2$, which can be identical or different, individually represent alkyl, cyanoalkyl, alkoxyalkyl, alkylthioalkyl, alkenyl, alkinyl or alkoxy, each having up to 10 C atoms, cycloalkyl or cycloalkenyl, each having up to 12 C atoms, aralkyl which has 1 or 2 carbon atoms in the alkyl part and 6 or 10 carbon atoms in the aryl part which is optionally substituted by halogen, or represent aryl having 6 or 10 carbon atoms, it being possible for the aryl radical to be substituted by 1 to 3 halogen atoms, 1 to 3 alkyl groups, each being optionally substituted by halogen (especially fluorine) and having 1 to 4 carbon atoms, nitro, cyano or alkoxy having 1 to 4 carbon atoms, or wherein the radicals R$^1$ and R$^2$, together with the nitrogen atom to which they are bonded, form an optionally partially unsaturated and/or benzofused monocyclic or bicyclic structure which has up to 15 carbon atoms and is optionally substituted by 1 to 3 alkyl groups, each having 1 to 5 carbon atoms, or wherein the radicals R$^1$ and R$^2$, together with the nitrogen atom to which they are bonded, form a saturated monocyclic structure which has up to 5 carbon atoms, is optionally substituted by 1 to 3 alkyl groups, each having 1 to 5 carbon atoms, and contains optionally a further nitrogen atom, oxygen atom or sulphur atom.

The invention particularly relates to compounds of the formula (I)

in which R$^1$ represents C$_1$–C$_5$-alkyl, cyanoethyl, C$_1$–C$_4$-alkoxy-ethyl, allyl, propargyl, 1-methyl-propargyl or 1,1-dimethyl-propargyl, and R$^2$ represents C$_1$–C$_5$-alkyl, C$_1$–C$_5$-alkoxy, cyanoethyl, C$_1$–C$_4$-alkoxy-ethyl, allyl, propargyl, 1-methyl-propargyl, 1,1-dimethylpropargyl, cyclopentyl, cyclohexyl, 3,4,6-trimethyl-cyclohexen-1-yl, benzyl, naphthyl or phenyl which is optionally substituted by 1 to 3 radicals (methyl, chlorine, fluorine, trifluoromethyl, methoxy, methylthio, trifluoromethoxy and/or trifluoromethylthio), or wherein the radicals R$^1$ and R$^2$, together with the nitrogen atom to which they are bonded, represent pyrrolidyl, monoalkyl- or dialkyl-pyrrolidyl having 1 to 3 carbon atoms per alkyl group, morpholinyl or dialkylmorpholinyl having 1 to 3 carbon atoms per alkyl group, piperidyl, monoalkyl-, dialkyl- or trialkylpiperidyl having 1 to 3 carbon atoms per alkyl group, perhydroazepinyl (hexamethyleneimino radical), the heptamethyleneimino radical, 1,2,3,4-tetrahydroindolyl, monoalkyl- or dialkyl-tetrahydroindolyl having up to 3 carbon atoms per alkyl group, perhydroindolyl, monoalkyl- or dialkylperhydroindolyl having 1 to 3 carbon atoms per alkyl group, 1,2,3,4-tetrahydroquinolyl or 1,2,3,4-tetrahydro-iso-quinolyl, monoalkyl- or dialkyl-1,2,3,4-tetrahydroquinolyl or -iso-quinolyl having 1 to 3 carbon atoms per alkyl group, perhydroquinolyl or perhydro-iso-quinolyl, monoalkyl- or dialkyl-perhydroquinolyl or -perhydroisoquinolyl having 1 to 3 carbon atoms per alkyl group.

If 5-chloro-3-fluorodichloromethyl-1,2,4-thiadiazole and, for example, hydroxyacetic acid N-methylanilide are used as starting materials, the course of the reaction in the process according to the invention can be represented by the following equation:

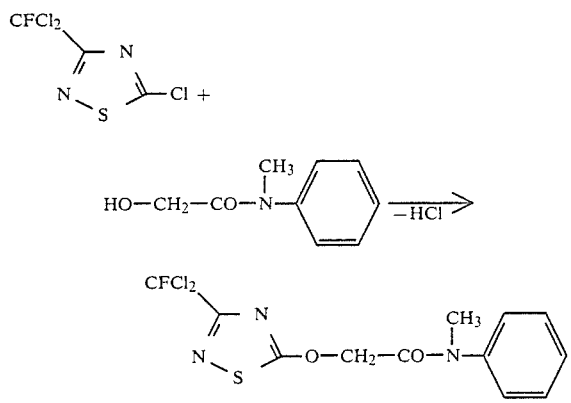

Formula (II) gives a definition of the hydroxyacetamides to be used as starting materials. In this formula, $R^1$ and $R^2$ preferably or particularly represent those radicals which have already been mentioned within the scope of the definitions of the substituents for formula (I) as being preferred or particularly preferred.

The following may be mentioned as examples of starting materials of the formula (II): hydroxyacetic acid dimethylamide, diethylamide, di-n-propylamide, diiso-propylamide, N-methyl-N-iso-propylamide, N-methyl-N-isobutyl-amide, N-methyl-N-sec.-butyl-amide, N-propyl-N-sec.-butyl-amide, N-methyl-N-(2-cyano-ethyl)-amide, di-(2-methoxy-ethyl)-amide, di-allyl-amide, N-methyl-N-propargyl-amide, N-methyl-N-(1-methyl-propargyl)-amide, dipropargyl-amide, N-methyl-N-cyclopentyl-amide, N-methyl-N-cyclohexyl-amide, N-methyl-N-(2-nitro-phenyl)-, N-methyl-N-(3-nitro-phenyl)- and N-methyl-N-(4-nitro-phenyl)-amide, N-methyl-N-(2-chloro-phenyl)-, N-methyl-N-(3-chlorophenyl)- and N-methyl-N-(4-chloro-phenyl)-amide, N-methyl-N-(3-nitro-6-methyl-phenyl)-amide, N-ethyl-anilide, N-ethyl-N-(2-nitro-phenyl)-, N-ethyl-(3-nitro-phenyl)- and N-ethyl-N-(4-nitro-phenyl)-amide, N-ethyl-N-(2-chlorophenyl)-, N-ethyl-N-(3-chloro-phenyl)- and N-ethyl-N-(4-chloro-phenyl)-amide, N-ethyl-N-(3-nitro-6-methylphenyl)-amide, N-propyl-anilide, N-propyl-N-(2-nitrophenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chlorophenyl)-amide, N-propyl-N-(2-methyl-phenyl)- N-propyl-N-(3-methyl-phenyl)- and N-propyl-N-(4-methyl-phenyl)-amide, N-propyl-N-(3-nitro-6-methyl-phenyl)-amide, N-butyl-anilide, N-methyl-N-naphth-1-ylamide, N-methyl-N-naphth-2-ylamide, N-ethyl-N-naphth-1-ylamide, N-ethyl-N-naphth-2-ylamide, N-methyl-N-benzylamide, N-ethyl-N-benzylamide, N-propyl-N-benzylamide, N-butyl-N-benzylamide, pyrrolidide, 1-methyl-pyrrolidide, morpholide, piperidide, 2-methyl-piperidide, 2-methyl-piperidide, 4-methyl-piperidide, 2,4-dimethyl-piperidide, 3,5-dimethyl-piperidide, 3,5-diethylpiperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2,-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroindolide, perhydroindolide, 2-methyl-perhydroindolide, 2,2-dimethyl-perhydroindolide, 2-methyl-1,2,3,4-tetrahydroquinolide, perhydroquinolide, 2-methyl-perhydroquinolide, 1,2,3,4-tetrahydro-isoquinolide and perhydroisoquinolide; also N-methyl-N-(2-methylthio-phenyl)-, N-methyl-N-(3-methylthiophenyl)- and N-methyl-N-(4-methylthio-phenyl)-amide, N-methyl-N-(2-fluorophenyl)-, N-methyl-N-(3-fluorophenyl)- and N-methyl-N-(4-fluorophenyl)-amide; N-methyl-N-2-trifluoromethylphenyl)-, N-methyl-N-(3-trifluoromethylphenyl)- and N-methyl-N-(4-trifluoromethylphenyl)-amide; N-methyl-N-(2-trifluoromethoxyphenyl)-, N-methyl-N-(3-trifluoromethoxyphenyl)- and N-methyl-N-(4-trifluoromethoxyphenyl)-amide; and N-methyl-N-(2-trifluoroethylphenyl)-amide.

Hydroxy-carboxamides of the formula (II) are known (see U.S. Pat. No. 3,399,988; and DE-OS (German Published Specifications) Nos. 2,201,432 and 2,647,481). They can be prepared, as shown in the equation below, using chloroacetyl chloride as the starting material:

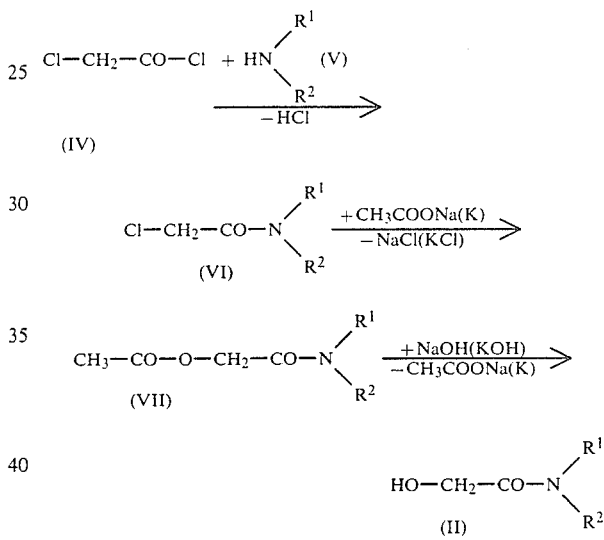

For this purpose, chloroacetyl chloride, which is known from the literature and is of the formula (IV), is first converted into the corresponding chloroacetamides of the formula (VI), using amines of the formula (V), wherein $R^1$ and $R^2$ have the meaning given above, if appropriate in the presence of an acid-binding agent, such as, for example, triethylamine, and if appropriate using an inert diluent, such as, for example, 1,2-dichloroethane, at temperatures between $-20°$ and $100°$ C., preferably between $-10°$ and $50°$ C. These products are worked up according to customary methods, by washing with water, drying the organic phase and distilling off the solvent.

The compounds of the formula (VI) are reacted with sodium acetate or potassium acetate, if appropriate using a diluent, such as, for example, acetic acid or dimethylsulphoxide, at temperatures between $20°$ and $150°$ C., preferably between $50°$ and $120°$ C., to give the corresponding acetoxy-acetamides of the formula (VII). If in this reaction the products are obtained in crystalline form, they are isolated by filtering them off under suction. Otherwise, working up is effected according to customary methods, for example by distilling off the solvent in vacuo, taking up the residue in methylene chloride, washing the solution with water and distilling off the solvent.

By reaction with aqueous-alcoholic sodium hydroxide solution or potassium hydroxide solution at temperatures between 0° and 100° C., preferably between 10° and 50° C., the compounds of the formula (VII) can be deacylated to give the compounds of the formula (II). To isolate the products, the solvents are distilled off in vacuo, the residue is extracted with an organic solvent, such as, for example, methylene chloride or ethyl acetate, the solution is dried and the solvent is distilled off.

Formula (III) gives a definition of the fluorine-containing 5-chloro-3-trihalogenomethyl-1,2,4-thiadiazoles to be used as starting materials. The compound (III) with $X=CF_3$ [5-chloro-3-trifluoromethyl-1,2,4-thiadiazole (IIIc)] and a process for its preparation are known (see J. Org. Chem. 27, pages 2589–2592 (1962). This compound can be prepared by reacting 5-chloro-3-trichloromethyl-1,2,4-thiadiazole (IV) (see also U.S. Pat. No. 3,260,588) with antimony trifluoride.

The compounds of the formula (III) with $X=CFCl_2$ and with $X=CF_2Cl$ have not been described hitherto. They can be prepared by a new inventive process, wherein the previously known 5-chloro-3-trichloromethyl-1,2,4-thiadiazole of the formula

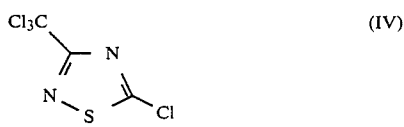

is reacted, in a pressure-tight vessel, with excess, anhydrous hydrogen fluoride, at temperatures between 100° and 180° C. and under pressures of up to about 50 bar, and the products are isolated by fractional distillation.

In this process, 8–30 mols, preferably 15–20 mols, of hydrogen fluoride are employed in general per mol of the compound (IV).

In the Cl/F exchange reaction which takes place, the compound (III) with $X=CFCl_2$ [5-chloro-3-fluorodichloromethyl-1,2,4-thiadiazole (IIIa)] is preferentially formed in the temperature range of 100°–140° C.

In the temperature range of 140°–180° C., the compound (III) with $X=CF_2Cl$ [5-chloro-3-difluorochloromethyl-1,2,4-thiadiazole (IIIb)] is preferentially formed.

In this reaction, in the temperature range of about 160°–180° C., the known compound (IIIc) is additionally formed in a small amount of about 2–4%, and can likewise be separated off by fractional distillation.

Furthermore, it has been found that the compound (IIIc) is obtained in good yields by a process in which the compound (IIIa) or (IIIb), or a mixture of these compounds is reacted with antimony trifluoride in the presence of catalytic amounts of antimony pentachloride. The reactants are combined at room temperature, the reaction mixture is heated to a final temperature of about 160° C., and a drop in temperature to about 130° C., corresponding to the boiling point of the product (IIIc) formed, is finally observed. In carrying out this subsequent fluorination, the antimony trifluoride (SbF₃) is employed in an amount of 10–15 mol %, per mol of compound (IIIa) or (IIIb), in excess of the particular theoretically calculated stoichiometric amount. The catalyst SbCl₅ is employed in amounts of 1–6% by weight, preferably of 3 to 5% by weight, relative in each case to the amount of SbF₃ used.

The reactions described for the preparation of the starting materials (IIIa), (IIIb) and (IIIc) can be summarized by the following equation:

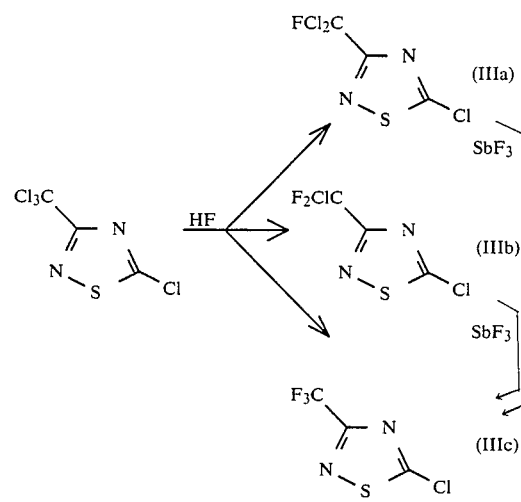

Further details in this connection are to be found in the preparation examples.

The process for the preparation of the new compounds of the formula (I) is preferably carried out using suitable solvents or diluents. Suitable solvents or diluents are virtually all inert organic solvents. These include, in particular, alcohols, such as methanol, ethanol, n- and iso-propanol, n-, iso-, sec.- and tert.- butanol, ethers, such as diethyl ether, dibutyl ether, tetrahydrofuran, diglyme and dioxane, ketones, such as acetone, methyl ethyl ketone, methyl isopropyl ketone and methyl isobutyl ketone, nitriles, such as acetonitrile and propionitrile, and the highly polar solvents dimethylformamide, dimethylsulphoxide, sulpholane and hexamethylphosphoric acid triamide.

Virtually all acid-binding agents which can customarily be used can be employed as acid acceptors: these include, in particular, alkali metal and alkaline earth metal hydroxides or oxides, such as sodium hydroxide, potassium hydroxide and in particular lithium hydroxide, and calcium oxide or calcium hydroxide, alkali metal and alkaline earth metal carbonates, such as sodium carbonate, potassium carbonate and calcium carbonate, alkali metal alcoholates, such as sodium methylate, ethylate and tert.-butylate, and potassium methylate, ethylate and tert.-butylate, and also aliphatic, aromatic or heterocyclic amines, such as triethylamine, dimethylaniline, dimethylbenzylamine, pyridine, diazabicyclooctane and diazabicycloundecane.

In the process according to the invention for the preparation of the active compounds (I), the reaction temperature can be varied within a relatively wide range. In general, the reaction is carried out at between −50° and +150° C., preferably at −20° to +100° C. The process according to the invention is carried out in general under normal pressure.

In carrying out the process according to the invention, 1.0 to 1.5 mols of hydroxyacetamide of the formula (II) are employed per mol of 5-chloro-3-trihalogenomethyl-1,2,4-thiadiazole of the formula (III). The reaction is carried out in general in a suitable diluent, and the reaction mixture is stirred at the required temperature for several hours.

The isolation of the products is effected by customary methods: if appropriate, a part of the diluent is distilled off under reduced pressure, and the remainder of the reaction mixture is poured into water. If the products are obtained in crystalline form in this process, they are isolated by filtering them off under suction. Otherwise, the organic products are extracted with a water-immiscible solvent, such as, for example, toluene or methylene chloride; after the solution has been washed and dried, the solvent is then distilled off in vacuo from the organic phase. The products which remain are characterized by their melting point or their refractive index.

The active compounds according to the invention can be used as defoliants, desiccants, agents for destroying broad-leaved plants, and especially as weedkillers. By weeds, in the broadest sense, there are to be understood all plants which grow in locations where they are undesired. Whether the substances according to the invention act as total or selective herbicides depends esssentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon cultures of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention exhibit, in addition to a very good action against monocotyledon weeds, a good herbicidal action in the case of dicotyledon weeds. The active compounds according to the invention can be used selectively in various cultures, especially in dicotyledon crop plants, such as, for example, cotton, as well as in rice and cereals.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene choride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphetes, arylsulphonates, as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.01 and 95% by weight of active compound, preferably between 0.5 and 90%.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially before the nature of the desired effect. In general, the amounts used are between 0.01 and 10 kg of active compound per ha, preferably between 0.1 and 5 kg/ha.

The compounds according to the invention, when applied in low dosages, also exhibit a plant growth regulating activity.

The examples which follow serve to illustrate the invention further.

PREPARATION EXAMPLES

EXAMPLE 1

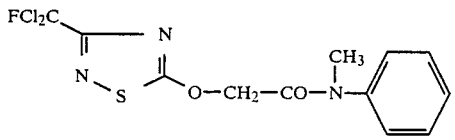

13 g (0.05 mol) of 5-chloro-3-fluorodichloromethyl-1,2,4-thidiazole are added to a mixture which comprises 8.2 g (0.05 mol) of hydroxyacetic acid N-methylanilide, 3.1 g (0.05 mol) of potassium hydroxide powder and 80 ml of iso-propanol and has been cooled to $-10°$ C., and the reaction mixture is stirred for 4 hours at $-10°$ C. Thereafter, the mixture is diluted with water, and the product is filtered off under suction. 13 g (74% of theory) of (3-fluorodichloromethyl-1,2,4-thiadiazol-5-yl)-oxyacetic acid N-methylanilide are obtained in the form of white crystals of melting point 67° C.

EXAMPLE 2

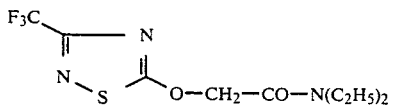

5.6 g (0.03 mol) of 5-chloro-3-trifluoromethyl-1,2,4-thiadiazole are added to a mixture which comprises 4 g (0.03 mol) of hydroxyacetic acid diethylamide, 1.9 g (0.03 mol) of potassium hydroxide powder and 80 ml of isopropanol and has been cooled to $-10°$ C. The reaction mixture is stirred for 10 hours at $-10°$ C. and poured into water, and the product is filtered off under suction. 4 g (47% of theory) of (3-trifluoromethyl-1,2,4-thiadiazol-5-yl)-oxyacetic acid diethylamide are obtained in the form of white crystals of melting point 60° C.

The compounds of the formula (I) which are listed in Table 1 below can be prepared analogously to Example 1 and 2.

TABLE 1

![Structure (I)a: X-thiadiazole-O-CH2-CO-N(R1)(R2)]

| Compound No. | —X | —N(R1)(R2) | Melting point °C./Refractive index $n_D^{20}$ |
|---|---|---|---|
| 3 | —CF₂Cl | —N(CH₃)(phenyl) | 75 |
| 4 | —CF₃ | —N(CH₃)(phenyl) | 91 |
| 5 | —CF₃ | —N(CH₃)(3-CF₃-phenyl) | 103 |
| 6 | —CF₃ | 2-methylpiperidin-1-yl | 76 |
| 7 | —CF₃ | hexamethyleneimin-1-yl | 76 |
| 8 | —CF₃ | 2-ethylpiperidin-1-yl | 57 |
| 9 | —CF₃ | 4-methylpiperidin-1-yl | 70 |
| 10 | —CF₃ | —N(CH₃)(2-methylphenyl) with CH₃ on N | 41 |
| 11 | —CFCl₂ | —N(C₂H₅)₂ | 48 |
| 12 | —CFCl₂ | 3-methylpiperidin-1-yl | $n_D^{20}$:1.5251 |

TABLE 1-continued (I)a

Structure: X-C(=N-N=S-N)-O-CH$_2$-CO-N(R$^1$)(R$^2$) (1,2,5-thiadiazole)

| Compound No. | −X | −N(R$^1$)(R$^2$) | Melting point °C./Refractive index $n_D^{20}$ |
|---|---|---|---|
| 13 | −CFCl$_2$ | N(CH$_3$)(3-methylphenyl) | $n_D^{20}$:1.5458 |
| 14 | −CFCl$_2$ | N(CH$_3$)(4-methylphenyl) | 112 |
| 15 | −CFCl$_2$ | hexamethyleneimino (azepan-1-yl) | 88 |
| 16 | −CFCl$_2$ | N(C$_2$H$_5$)(phenyl) | 48 |
| 17 | −CFCl$_2$ | 3-ethylpiperidin-1-yl | 64 |
| 18 | −CFCl$_2$ | N(CH$_3$)(2-methylphenyl) | 50 |
| 19 | −CFCl$_2$ | N(CH$_3$)(2-methyl-5-nitrophenyl) | 90 |
| 20 | −CF$_3$ | N(CH$_3$)(2-SCH$_3$-phenyl) | |
| 21 | −CFCl$_2$ | N(CH$_3$)(3-SCH$_3$-phenyl) | |
| 22 | −CF$_2$Cl | N(CH$_3$)(2-SCH$_3$-phenyl) | |
| 23 | −CF$_3$ | N(CH$_3$)(4-SCH$_3$-phenyl) | |
| 24 | −CFCl$_2$ | N(CH$_3$)(4-SCH$_3$-phenyl) | |
| 25 | −CF$_2$Cl | N(CH$_3$)(4-SCH$_3$-phenyl) | |
| 26 | −CF$_3$ | N(CH$_3$)(3-SCH$_3$-phenyl) | |
| 27 | −CFCl$_2$ | N(CH$_3$)(3-SCH$_3$-phenyl) | |
| 28 | −CF$_2$Cl | N(CH$_3$)(3-SCH$_3$-phenyl) | |
| 29 | −CF$_3$ | N(CH$_3$)(2-CF$_3$-phenyl) | |
| 30 | −CFCl$_2$ | N(CH$_3$)(2-CF$_3$-phenyl) | |

TABLE 1-continued $$\underset{N \diagdown S}{\overset{X}{\underset{\|}{\bigg\|}}} \diagdown O-CH_2-CO-N \diagdown \overset{R^1}{R^2} \quad (I)a$$

| Compound No. | -X | -N(R¹)(R²) | Melting point °C./Refractive index $n_D^{20}$ |
|---|---|---|---|
| 31 | -CF₂Cl | N(CH₃)-(2-CF₃-C₆H₄) | |
| 32 | -CF₃ | N(CH₃)-(4-CF₃-C₆H₄) | |
| 33 | -CFCl₂ | N(CH₃)-(4-CF₃-C₆H₄) | |
| 34 | -CF₂Cl | N(CH₃)-(4-CF₃-C₆H₄) | |
| 35 | -CF₃ | N(CH₃)-(2-F-C₆H₄) | |
| 36 | -CFCl₂ | N(CH₃)-(2-F-C₆H₄) | |
| 37 | -CF₂Cl | N(CH₃)-(2-F-C₆H₄) | |
| 38 | -CF₃ | N(CH₃)-(3-F-C₆H₄) | |
| 39 | -CFCl₂ | N(CH₃)-(3-F-C₆H₄) | |
| 40 | -CF₂Cl | N(CH₃)-(3-F-C₆H₄) | |
| 41 | -CF₃ | N(CH₃)-(4-F-C₆H₄) | |
| 42 | -CFCl₂ | N(CH₃)-(4-F-C₆H₄) | |
| 43 | -CF₂Cl | N(CH₃)-(4-F-C₆H₄) | |
| 44 | -CF₃ | N(CH₃)-(2-Cl-C₆H₄) | |
| 45 | -CFCl₂ | N(CH₃)-(2-Cl-C₆H₄) | |
| 46 | -CF₂Cl | N(CH₃)-(2-Cl-C₆H₄) | |
| 47 | -CF₃ | N(CH₃)-(3-Cl-C₆H₄) | |
| 48 | -CFCl₂ | N(CH₃)-(3-Cl-C₆H₄) | |

TABLE 1-continued $$\text{(I)a}$$

| Compound No. | —X | —N(R¹)(R²) | Melting point °C./Refractive index $n_D^{20}$ |
|---|---|---|---|
| 49 | —CF₂Cl | —N(CH₃)(3-chlorophenyl) | |
| 50 | —CF₃ | —N(CH₃)(4-chlorophenyl) | |
| 51 | —CFCl₂ | —N(CH₃)(4-chlorophenyl) | |
| 52 | —CF₂Cl | —N(CH₃)(4-chlorophenyl) | |
| 53 | —CF₃ | —N(CH₃)(2,4-dichlorophenyl) | |
| 54 | —CFCl₂ | —N(CH₃)(2,4-dichlorophenyl) | |
| 55 | —CF₂Cl | —N(CH₃)(2,4-dichlorophenyl) | |
| 56 | —CF₃ | —N(CH₃)(2-nitrophenyl) | |
| 57 | —CFCl₂ | —N(CH₃)(2-nitrophenyl) | |
| 58 | —CF₂Cl | —N(CH₃)(2-nitrophenyl) | |
| 59 | —CF₃ | —N(CH₃)(3-nitrophenyl) | |
| 60 | —CFCl₂ | —N(CH₃)(3-nitrophenyl) | |
| 61 | —CF₂Cl | —N(CH₃)(3-nitrophenyl) | |
| 62 | —CF₃ | —N(CH₃)(4-nitrophenyl) | |
| 63 | —CFCl₂ | —N(CH₃)(4-nitrophenyl) | |
| 64 | —CF₂Cl | —N(CH₃)(4-nitrophenyl) | |
| 65 | —CF₃ | —N(CH₃)(2-SCF₃-phenyl) | |
| 66 | —CFCl₂ | —N(CH₃)(2-SCF₃-phenyl) | |

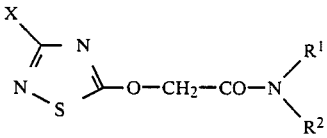
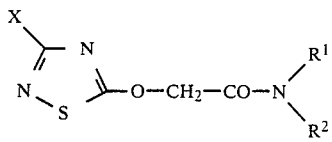

TABLE 1-continued $$\text{(I)a}$$

Structure: X-C(=N-N=C(S))-O-CH₂-CO-N(R¹)(R²) [3-substituted-1,2,4-thiadiazole]

| Compound No. | —X | —N(R¹)(R²) | Melting point °C./Refractive index $n_D^{20}$ |
|---|---|---|---|
| 87 | —CFCl₂ | N-methyl-(3,3,5-trimethylcyclohex-1-enyl)amino | |
| 88 | —CF₂Cl | N-methyl-(3,3,5-trimethylcyclohex-1-enyl)amino | |
| 89 | —CF₃ | N-methyl-(cyclohex-1-enyl)amino | 50 |
| 90 | —CFCl₂ | N-methyl-(cyclohex-1-enyl)amino | |
| 91 | —CF₂Cl | N-methyl-(cyclohex-1-enyl)amino | |
| 92 | —CF₃ | —N(CH₃)₂ | 60 |
| 93 | —CF₃ | 4-methylpiperidino | 43 |
| 94 | —CF₃ | 3,5-dimethylpiperidino | 52 |
| 95 | —CF₃ | N-ethyl-phenylamino | ($n_D^{20}$:1.5094) |
| 96 | —CF₃ | N-ethyl-(4-methylphenyl)amino | 50 |
| 97 | —CF₃ | N-methyl-(2-methyl-4-nitrophenyl)amino | 115 |
| 98 | —CF₃ | N-methyl-benzylamino | 48 |
| 99 | —CF₂Cl | —N(CH₃)₂ | 55 |
| 100 | —CF₂Cl | 2-methylpiperidino | ($n_D^{20}$:1.4979) |
| 101 | —CF₂Cl | —N(C₂H₅)₂ | 46 |
| 102 | —CF₂Cl | —N(CH₂—CH=CH₂)₂ | ($n_D^{20}$:1.5029) |
| 103 | —CF₂Cl | hexamethyleneimino (azepan-1-yl) | 80 |
| 104 | —CF₂Cl | 4-methylpiperidino | 54 |
| 105 | —CF₂Cl | N-methyl-(2-methylphenyl)amino | 48 |

Preparation of the starting materials of the formula (III)

(A) Preparation of 3-fluorodichloromethyl-5-chloro-1,2,4-thiadiazole (IIIa) and 3-difluorochloromethyl-5-chloro-1,2,4-thiadiazole (IIIb) 4,520 g of 3-trichloromethyl-5-chloro-1,2,4-thiadiazole (IV) and 3,800 ml of hydrogen fluoride (absolute) are initially introduced into an autoclave, at 0° C.

After the autoclave has been closed, the pressure of the protective nitrogen gas is brought to 2 bar, and the mixture is heated to an internal temperature of 140° C., while stirring. As a result of the Cl/F exchange which takes place in the reaction mixture, hydrogen chloride is liberated, and the pressure increases accordingly. A pressure of about 28 bar is maintained by releasing the pressure via a regulating valve. The reaction is complete after 5 hours. The pressure-release valve is set an increased pressure of 38 bar, and the mixture is then heated to 160° C. and allowed to react further for 6 hours at this temperature. Thereafter, the mixture is allowed to cool, the pressure is released and the autoclave content is worked up by distillation.

After first runnings of unconsumed hydrogen fluoride, the following fractions are obtained:

Fraction 1

77 g, up to a boiling point of 54° C./14 mbar; contains about 40% of 3-trifluoromethyl-5-chloro-1,2,4-thiadiazole (IIIc). (IIIc) can be isolated by redistillation of this fraction; boiling point: 127° C.; $n_D^{20}$: 1.4360.

Fraction 2

2,280 g of 3-difluorochloromethyl-5-chloro-1,2,4-thiadiazole (IIIb); boiling point: 55°–56° C./14 mbar; $n_D^{20}$: 1.4822.

Fraction 3

83 g of an intermediate cut.

Fraction 4

1,070 g of 3-fluorodichloromethyl-5-chloro-1,2,4-thiadiazole (IIIa); boiling point: 84° C./16 mbar; $n_D^{20}$: 1.5272.

(B) Preparation of 3-trifluoromethyl-5-chloro-1,2,4-thiadiazole (IIIc):

221.5 g of 3-fluorodichloromethyl-5-chloro-1,2,4-thiadiazole (IIIa) and 144 g of antimony trifluoride (SbF₃) are initially introduced into a stirred flask, and heated to 155° C. Thereafter, the mixture is cooled to 50° C., 3 ml of antimony pentachloride (SbCl₅) are added, and the mixture is again warmed slowly. At about 100° C., a clearly exothermic reaction takes place and the mixture becomes fluid. The mixture is stirred for a further hour at an internal temperature of 135°–137° C., and is then worked up by distillation. The distillate is washed with dilute hydrochloric acid and dried; if desired, it can be redistilled.

Yield: 174 g (92.3% of theory) of 3-trifluoromethyl-5-chloro-1,2,4-thiadiazole (IIIc); $n_D^{20}$: 1.4370. Renewed distillation gives a boiling point of 126°–128° C. for (IIIc); $n_D^{20}$: 1.4365.

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, an excellent activity is shown by, for example, the following compounds according to the preparation examples: (1) and (2).

EXAMPLE B

Growth inhibitor for barley

Solvent: 30 parts by weight of dimethylformamide

Emulsifier: 1 part by weight polyoxyethylene-sorbitan-monolaurate

To produce a suitable preparation of active compound, 1 part by weight of active compound is mixed with the stated amount of solvent, the stated amount of emulsifier is added and the concentrate is diluted with water to the desired concentration.

Barley plants are grown in a greenhouse until the 2-leaf stage is reached. At this stage the plants are sprayed with the preparations of active compound until they are dripping wet. After 3 weeks the growth of all the plants is measured and the growth inhibition is calculated as a percentage of the growth of the control plants. 100% growth inhibition signifies a standstil in growth and 0% denotes growth corresponding to that of the control plants.

In this test, an excellent activity is shown by, for example, the following compounds according to the preparation example: (2).

EXAMPLE C

Growth inhibitor for soy beans

Solvent: 30 parts by weight of dimethylformamide

Emulsifier: 1 part by weight polyoxyethylene-sorbitan-monolaurate

To produce a suitable preparation of active compound, 1 part by weight of active compound is mixed with the stated amount of solvent, the stated amount of emulsifier is added and the concentration is diluted with water to the desired concentration.

Soy bean plants are grown in a greenhouse until the first leaf has fully developed. At this stage the plants are sprayed with the preparations of active compound until they are dripping wet. After 3 weeks the growth of all the plants is measured and the growth inhibition is calculated as a percentage of the growth of the control plants.

100% growth inhibition denotes a standstil in growth and 0% denotes growth corresponding to that of the control plants.

In this test, an excellent activity is shown by, for example, the following compounds according to the preparation example: (2).

What is claimed is:

1. A substituted 3-trihalogenomethyl-1,2,4-thiadiazol-5-yl-oxyacetamide of the formula $$\begin{array}{c} X \\ \diagdown \\ N \\ \diagup\diagup \\ N \diagdown _S \diagup \diagdown O-CH_2-CO-N \diagup^{R^1} _{R^2} \end{array}$$

in which

X represents —CFCl₂, —CF₂Cl or —CF₃ and

R¹ and R², which can be identical or different, individually represent alkyl, cyanoalkyl, alkoxyalkyl, alkylthioalkyl, alkenyl, alkinyl or alkoxy, each having up to 10 C atoms, cycloalkyl or cycloalkenyl, each having up to 12 C atoms, aralkyl which has 1 or 2 carbon atoms in the alkyl part and 6 or 10 carbon atoms in the aryl part, which is optionally substituted by halogen, or represent aryl having 6 or 10 carbon atoms, it being possible for the aryl radical to be substituted by 1 to 3 halogen atoms, 1 to 3 alkyl groups, each being optionally substituted by halogen and having 1 to 4 carbon atoms, nitro, cyano or alkoxy having 1 to 4 carbon atoms, or wherein the radicals $R^1$ and $R^2$, together with the nitrogen atom to which they are bonded, form an unsaturated and/or benzofused monocyclic or bicyclic structure which has up to 15 carbon atoms as the only other ring atoms and is optionally substituted by 1 to 3 alkyl groups, each having 1 to 5 carbon atoms, or by two geminal alkoxy groups, each having 1 to 3 carbon atoms, or wherein the radicals $R^1$ and $R^2$, together with the nitrogen atom to which they are bonded, form a saturated monocyclic structure which has up to 6 carbon atoms, is optionally substituted by 1 to 3 alkyl groups, each having 1 to 5 carbon atoms, and optionally contains a further nitrogen atom, oxygen atom or sulphur atom in the ring.

2. A compound according to claim 1, in which $R^1$ represents $C_1-C_5$-alkyl, cyanoethyl, $C_1-C_4$-alkoxy-ethyl, allyl, propargyl, 1-methyl-propargyl or 1,1-dimethyl-propargyl, and $R^2$ represents $C_1-C_5$-alkyl, $C_1-C_5$-alkoxy, cyanoethyl, $C_1-C_4$-alkoxy-ethyl, allyl, propargyl, 1-methyl-propargyl, 1,1-dimethylpropargyl, cyclopentyl, cyclohexyl, 3,4,6-trimethyl-cyclohexen-1-yl, benzyl, naphthyl or phenyl which is optionally substituted by 1 to 3, chlorine, fluorine, trifluoromethyl, methoxy, methylthio, trifluoromethoxy and/or trifluoromethylthio radicals, or wherein the radicals $R^1$ and $R^2$, together with the nitrogen atom to which they are bonded, represent pyrrolidyl, monoalkyl- or dialkyl-pyrrolidyl having 1 to 3 carbon atoms per alkyl group, morpholinyl or dialkylmorpholinyl having 1 to 3 carbon atoms per alkyl group, piperidyl, monoalkyl-, dialkyl- or trialkylpiperidyl having 1 to 3 carbon atoms per alkyl group, perhydroazepinyl (hexamethyleneimino radical), the heptamethyleneimino radical, 1,2,3,4-tetrahydroindolyl, monoalkyl- or dialkyl-tetrahydroindolyl having up to 3 carbon atoms per alkyl group, perhydroindolyl, monoalkyl- or dialkylperhydroindolyl having 1 to 3 carbon atoms per alkyl group, 1,2,3,4-tetrahydroquinolyl or 1,2,3,4-tetrahydro-iso-quinolyl, monoalkyl- or dialkyl-1,2,3,4-tetrahydroquinolyl or -iso-quinolyl having 1 to 3 carbon atoms per alkyl group, perhydroquinolyl or perhydro-isoquinolyl, monoalkyl- or dialkyl-perhydroquinolyl or -perhydroisoquinolyl having 1 to 3 carbon atoms per alkyl group.

3. A compound according to claim 1, wherein such compound is (3-fluorodichloromethyl-1,2,4-thiadiazol-5-yl)-oxyacetic acid N-methylanilide of the formula

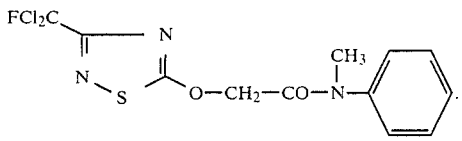

4. A compound according to claim 1, wherein such compound is (3-trifluoromethyl-1,2,4-thiadiazol-5-yl)-oxyacetic acid diethylamide of the formula

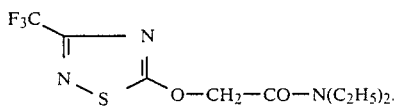

5. A herbicidal composition comprising a herbicidally effective amount of a compound according to claim 1 in admixture with a diluent.

6. A method of combatting unwanted vegetation which comprises administering to such vegetation or to a location in which it is to be grown a herbicidally effective amount of a compound according to claim 1.

7. The method according to claim 6, wherein such compound is (3-fluorodichloromethyl-1,2,4-thiadiazol-5-yl)-oxyacetic acid N-methylanilide of the formula

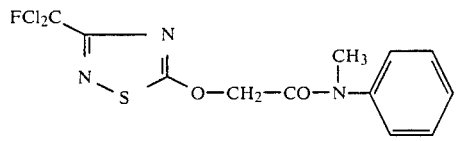

or (3-trifluoromethyl-1,2,4-thiadiazol-5-yl)-oxyacetic acid diethylamide of the formula

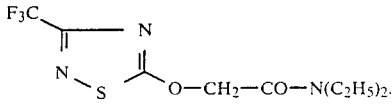

8. A 5-chloro-3-trihalogenomethyl-1,2,4-thiadiazole of the formula

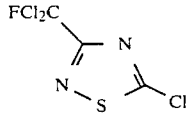

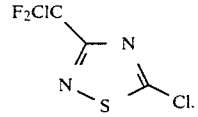

* * * * *